United States Patent
Breit et al.

(10) Patent No.: US 10,705,096 B2
(45) Date of Patent: Jul. 7, 2020

(54) PROGNOSING MORTALITY IN PATIENTS WITH CHRONIC KIDNEY DISEASE BY DETECTING MACROPHAGE INHIBITORY CYTOKINE-1 (MIC-1)

(71) Applicant: St Vincent's Hospital Sydney Limited, Darlinghurst, New South Wales (AU)

(72) Inventors: Samuel Norbert Breit, New South Wales (AU); David Alexander Brown, New South Wales (AU)

(73) Assignee: ST VINCENT'S HOSPITAL SYDNEY LIMITED, Darlinghurst (AU)

( * ) Notice: Subject to any disclaimer, the term of this patent is extended or adjusted under 35 U.S.C. 154(b) by 0 days.

(21) Appl. No.: 15/266,426

(22) Filed: Sep. 15, 2016

(65) Prior Publication Data

US 2017/0023587 A1 Jan. 26, 2017

Related U.S. Application Data (63) Continuation of application No. 14/173,191, filed on Feb. 5, 2014, now abandoned, which is a continuation of application No. 12/998,484, filed as application No. PCT/AU2009/001413 on Oct. 29, 2009, now abandoned.

(30) Foreign Application Priority Data

Oct. 31, 2008 (AU) .................................. 2008905617

(51) Int. Cl.
*G01N 33/53* (2006.01)
*G01N 33/68* (2006.01)
*A61M 1/36* (2006.01)

(52) U.S. Cl.
CPC ....... *G01N 33/6863* (2013.01); *A61M 1/3624* (2013.01); *G01N 33/6893* (2013.01); *G01N 2333/52* (2013.01); *G01N 2800/347* (2013.01); *G01N 2800/52* (2013.01)

(58) Field of Classification Search
CPC ................................................. G01N 33/6863
See application file for complete search history.

(56) References Cited

U.S. PATENT DOCUMENTS

| | | |
|---|---|---|
| 5,994,102 A | 11/1999 | Hudson et al. |
| 6,051,424 A | 4/2000 | Kato et al. |
| 6,180,602 B1 | 1/2001 | Kato et al. |
| 6,420,543 B1 | 7/2002 | Lee et al. |
| 6,465,181 B2 | 10/2002 | Billing-Medel et al. |
| 6,500,638 B2 | 12/2002 | Hudson et al. |
| 6,521,227 B1 | 2/2003 | Hudson et al. |
| 7,157,235 B2 | 1/2007 | Breit et al. |
| 7,282,351 B2 | 10/2007 | Hudson et al. |
| 7,919,084 B2 | 4/2011 | Breit et al. |
| 2003/0113744 A1 | 6/2003 | O'Toole et al. |

FOREIGN PATENT DOCUMENTS

| | | |
|---|---|---|
| JP | 07-250688 | 10/2007 |
| JP | 07-258293 | 10/2007 |
| JP | 2007-532586 A | 11/2007 |
| JP | 2011-501136 A | 1/2011 |
| JP | 2011-502106 | 1/2011 |
| JP | 2011-523051 A | 8/2011 |
| WO | WO 94/03599 A1 | 2/1994 |
| WO | WO 95/14772 A1 | 6/1995 |
| WO | WO 96/18730 A1 | 6/1996 |
| WO | WO 97/00958 A1 | 1/1997 |
| WO | WO 97/36926 A1 | 10/1997 |
| WO | WO 99/06445 A1 | 2/1999 |
| WO | WO 99/21011 A1 | 4/1999 |
| WO | WO 00/70051 A1 | 11/2000 |
| WO | WO 01/81928 A1 | 11/2001 |
| WO | WO 02/059373 A2 | 8/2002 |
| WO | WO 03/093794 A2 | 11/2003 |
| WO | WO 2005/099746 A1 | 10/2005 |
| WO | WO 2007/047458 A2 | 4/2007 |
| WO | WO 2007/112330 A2 | 10/2007 |
| WO | WO 2009/021293 A1 | 2/2009 |
| WO | WO 2009/046495 A1 | 4/2009 |
| WO | WO 2009/052557 A1 | 4/2009 |
| WO | WO 2009/052573 A1 | 4/2009 |
| WO | WO 2009/141357 A1 | 11/2009 |
| WO | WO 2011/050407 A1 | 5/2011 |

OTHER PUBLICATIONS

Brown et al., "Antibody-Based Approach to High-Volume Genotyping for MIC-1 Polymorphism" *Biotechnique*, vol. 33, No. 1: pp. 118-126 (Jul. 2002).

Canadian Office Action issued in Appln. No. 2,740,632 dated Nov. 1, 2017.

Alberts, B., et al; Molecular Biology of the Cell, 3$^{rd}$ ed.; *Garland Publishing Inc.*, pp. 1255-1272 (1994).

Li, Pei-Xiang, et al; "Placental Transforming Growth Factor-β is a Downstream Mediator of the Growth Arrest and Apoptotic Response of Tumor Cells to DNA Damage and p53 Overexpression"; *J. Biological Chemistry*, vol. 275, No. 26: 20127-20135 (2000).

(Continued)

*Primary Examiner* — Prema M Mertz (74) *Attorney, Agent, or Firm* — Nixon & Vanderhye P.C.

(57) ABSTRACT

The present invention relates to methods of prognosing the survival of a diseased subject, particularly a subject with chronic kidney disease (CKD), as well as selecting an end-stage renal disease subject for a kidney transplant. The methods involve detecting an elevated amount of macrophage inhibitory cytoking-1 (MID-1) in a test body sample from the diseased subject. A method of preventing or reducing the risk of death in a CKD subject which involves removing or inactivating MIC-1 present in the blood, plasma or serum of the subject, is also disclosed.

2 Claims, 2 Drawing Sheets

Specification includes a Sequence Listing.

(56) References Cited

OTHER PUBLICATIONS

Fairlie, W.D., et al; "Epitope Mapping of the Transforming Growth Factor-β Superfamily Protein, Macrophage Inhibitory Cytoking-1 (MIC-1): Identification of at Least five Distinct Epitope Specificities"; Biochemistry, 40: 65-73 (2001).
Harlow et al; "Antibodies, A Laboratory Manual"; Cold Spring Harbor Laboratory, p. 76 (1988).
Kuby, J.; "Immunology"; W.H. Freeman and Company; p. 125 (1992).
Whisstock, J.C., et al; "Prediction of protein function from protein sequence and structure"; Quarterly Reviews of Biophysics; 36: 307-340 (2003).
Fairlie, W.D., et al; "The Propeptide of the Transforming Growth Factor-β Superfamily Member, Macrophage Inhibitory Cytokine-1 (MIC-1), is a Multifunctional Domain That Can Facilitate Protein Folding and Secretion"; J. Biological Chemistry; 276: 16911-16918 (2001).
Yokoyama-Kobayashi, M., et al; "Human cDNA Encoding a Novel TGF-β Superfamily Protein Highly Expressed in Placenta"; J. Biochem, 122: 622-626 (1997).
Lawton, L.N., et al; "Identification of a novel member of the TGF-beta superfamily highly expressed in human placenta"; Gene, 203: 17-26 (1997).
Hillier, S.L., et al; "The Relationship of Amniotic Fluid Cytokines and Preterm Delivery, Amniotic Fluid Infection, Histologic Chorioamnionitis, and Chorioamnion Infection"; Obstetrics & Gynecology; 81: 941-948 (1993).
Hromas, R., et al; "Short sequence-paper, PLAB, a novel placental bone morphogenetic protein"; Biochimica et Biophysica Acta; 1354: 40-44 (1997).
Paralkar, V.M., et al; "Cloning and Characterization of a Novel Member of the Transforming Growth Factor-β/Bone Morphogenetic Protein Family"; J. Biol. Chemistry; 273: 13760-13767 (1998).
Moore, A.G., et al; "The Transforming Growth Factor-β Superfamily Cytokine Macrophage Inhibitory Cytokine-1 is Present in High Concentratinos in the Serum of Pregnant Women"; Journal of Clinical Endocrinology & Metabolism; 85: 4781-4788 (2000).
Fairlie, W.D., et al; "MIC-1 is a novel TGF-β superfamily cytokine associated with macrophage activation"; Journal of Leukocyte Biology, 65: 2-5 (1999).
Bootcov, M.R., et al; MIC-1, a novel macrophage inhibitory cytokine, is a divergent member of the TGF-β superfamily; Proc. Natl. Acad. Sci. USA; 94: 11514-11519 (1997).
Strelau, J., et al; "Growth/Differentiation Factor-15/Macrophage Inhibitory Cytokine-1 is a Novel Trophic Factor for Midbrain Dopaminergic Neurons In Vivo"; Journal of Neuroscience; 20:8597-8603 (2000).
Bottner, M., et al; "Characterization of the rat, mouse, and human genes of growth/differentiation factor-15/macrophage inhibiting cytokine-1 (GDF-15/MIC-1)"; Gene; 237: 105-111 (1999).
Bottner, M., et al; "Expression of a novel member of the TGF-β superfamily, growth/differentiation factor-15/macrophage-inhibiting cytokine-1 (GDF-15/MIC-1) in adult rat tissues"; Cell Tissue Research; 297: 103-110 (1999).
Bauskin, A.R., et al; "The propeptide of macrophage inhibitory cytokine (MIC-1), a TGF-β superfamily member, acts as a quality control determinant for correctly folded MIC-1"; The EMBO Journal, 19: 2212-2220 (2000).
Database EMBL Online; Accession No. R33078 (SP002199768) 2 pgs (2000).
Baoutina, A., et al; "Antioxidant Properties of Macrophages Toward Low-Density Lipoprotein"; Trends in Cardiovascular Medicine; 11: 1-7 (2001).

Ross, R.; "Atherosclerosis—An Inflammatory Disease"; New England Journal of Medicine; 340: 115-126 (1999).
Ridker, P.M., et al; Circulation; 101: 1767-1772 (2000).
Ridker, P.M., et al; "C-Reactive Protein and Other Markers of Inflammation in the Prediction of Cardiovascular Disease in Women"; The New England Journal of Medicine; 342: 836-843 (2000).
Brown, et al; The Lancet, 359: 2159-2163 (2002).
Xu et al; Circ Res.; 98: 342-350 (2006).
Sidney, S., et al; "Myocardial Infraction and Use of Low-Dose Oral Contraceptives, A Pooled Analysis of 2 US Studies"; Circulation; 98: 1058-1063 (1998).
Yudkin, J.S., et al; "Inflammation, obesity, stress and coronary heart disease: is interleukin-6 the link?" Atherosclerosis; 148: 209-214 (2000).
Hak, A.E., et al; "Increased plasma homocysteine after menopause"; Atherosclerosis; 149: 163-168 (2000).
Zhu, J., et al; "Effects of Total Pathogen Burden on Coronary Artery Disease Risk and C-Reactive Protein Levels"; American Journal of Cardiology; 85: 140-146 (2000).
Brown, D.A., et al; "Measurement of Serum Levels of Marcrophage Inhibitory Cytokine 1 Combined with Prostate-Specific Antigen Improves Prostate Cancer Diagnosis"; Clinical Cancer Research; 12: 89-96 (2006).
Bauskin, A.R., et al; "Role of Macrophage Inhibitory Cytokine-1 in Tumorigenesis and Diagnosis of Cancer"; Cancer Research; 66: 4983-4986 (2006).
Welsh, J.B., et al; "Large-scale delineation of secreted protein biomarkers overexpressed in cancer tissue and serum"; PNAS; 100: 3410-3415 (2003).
Welsh, J.B., et al; "Table 1. Genes encoding candidate secreted proteins overexpressed in carcinomas"; PNAS; 100: 3410-3415 (2003).
Nakamura, T., et al; "Quantitative analysis of macrophage inhibitory cytokine-1 (MIC-1) gene expression in human prostatic tissues"; British Journal of Cancer; 88: 1101-1104 (2003).
Rasiah, K.K., et al; "Aberrant Neuropeptide Y and Macrophage Inhibitory Cytokine-1 Expression Are Early Events in Prostate Cancer Development and Are Associated with Poor Prognosis"; Cancer Epidemiol Biomarkers Prevention; 15:711-716 (2006).
Brown, D.A., et al; "MIC-1 Serum Level and Genotype: Associations with Progress and Prognosis of Colorectal Carcinoma"; Clinical Cancer Research; 9: 2642-2650 (2003).
Baek, S.J., et al; "Dual Function of Nonsteroidal Anti-Inflammatory Drugs (NSAIDs): Inhibition of Cyclooxygenase and Induction of NSAID-Activated Gene"; The Journal of Pharmacology and Experimental Therapeutics; 301: 1126-1131 (2002).
Supplementary European Search Report, European Application No. EP 09822897.6-1223/2350669 PCT/AU2009001413 dated Apr. 12, 2012 (9 pgs).
Brown, D.A., et al; "MIC-1 Serum Level and Genotype: Associations with Progress and Prognosis of Colorectal Carcinoma"; Clinical Cancer Research, vol. 9, pp. 2642-2650 (2003).
Japanese Office Action issued in corresponding Japanese Patent Application No. 2011-533486, dated Feb. 21, 2013, 7 pgs.
Nature Medicine, vol. 13, No. 11, pp. 1333-1340 (2007).
Nephrol Dial Transplant, vol. 27, pp. 70-75 (2012).
Johnen, H., et al; "Tumor-induced anorexia and weight loss are mediated by the TGF-β superfamily cytokine MIC-1"; Nature Medicine, vol. 13, No. 11, pp. 1333-1340 (2007).
Breit, S.N., et al; "Macrophage inhibitory cytokine-1 (MIC-1/GDF15) and mortality in end-stage renal disease"; Nephrol Dial Transplant, vol. 27, pp. 70-75 (2012).
Brown et al., "Macrophage Inhibitory Cytokine 1: A New Prognostic Marker in Prostate Cancer"; National Institute of Health, Clin. Cancer Res., Nov. 1, 2009; 15(21): pp. 6658-6664.

FIGURE 1

(A) Wild type (H6) mature human MIC-1 polypeptide sequence

```
ARNGDHCPLG PGRCCRLHTV RASLEDLGWA DWVLSPREVQ VTMCIGACPS QFRAANMHAQ      60
IKTSLHRLKP DTVPAPCCVP ASYNPMVLIQ KTDTGVSLQT YDDLLAKDCH CI(SEQ ID NO:1) 112
```

(B) D6 mature human MIC-1 polypeptide sequence

```
ARNGDDCPLG PGRCCRLHTV RASLEDLGWA DWVLSPREVQ VTMCIGACPS QFRAANMHAQ      60
IKTSLHRLKP DTVPAPCCVP ASYNPMVLIQ KTDTGVSLQT YDDLLAKDCH CI(SEQ ID NO:2) 112
```

PROGNOSING MORTALITY IN PATIENTS WITH CHRONIC KIDNEY DISEASE BY DETECTING MACROPHAGE INHIBITORY CYTOKINE-1 (MIC-1)

This application is continuation of patent application Ser. No. 14/173,191, filed Feb 5, 2014 (pending), which is a continuation of application Ser. No. 12/998,484, filed May 17, 2011 (abandoned), which is a 371 of PCT/AU2009/001413, filed Oct. 29, 2009, which claims priority of Australian Patent Application No 2008905617, filed Oct. 31, 2008, the entire contents of each of which are hereby incorporated by reference.

FIELD OF THE INVENTION

The present invention relates to a method of prognosing the survival of a diseased subject. In particular, the invention relates to a method of prognosing the survival of a subject with chronic kidney disease.

INCORPORATION BY REFERENCE

This patent application refers to:
International Patent Application No PCT/AU01/00456 (WO 01/81928);
International Patent Application No PCT/AU2005/000525 (WO 2005/099746); and
International Patent Application No PCT/AU2008/001498 (WO 2009/046495);
in the following description. The entire content of each of these specifications is herein incorporated by reference.

BACKGROUND OF THE INVENTION

Figure 1:
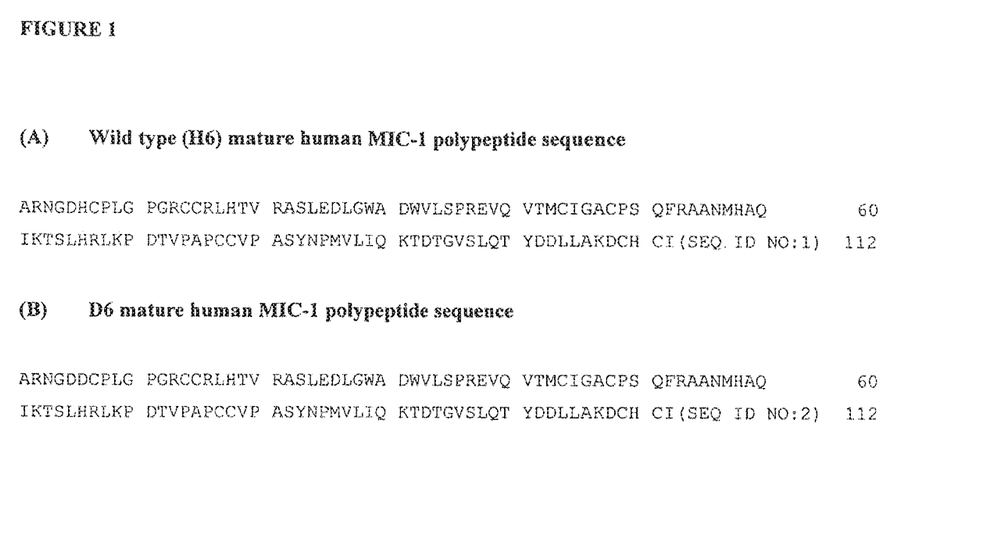
FIG. 1 provides (A) the amino acid sequence for the common or "wild type" mature human MIC-1 polypeptide; and (B) the amino acid sequence of a D6 mature human MIC-1 variant.

Macrophage inhibitory cytokine (MIC)-1 is a transforming growth factor-β (TGF-β) superfamily protein. MIC-1 was originally cloned as macrophage inhibitory cytokine-1 and later identified as placental transforming growth factor-β (PTGF-β), placental bone morphogenetic protein (PLAB), non-steroidal anti-inflammatory drug-activated gene 1 (NAG-1), prostate-derived factor (PDF) and growth development factor-15 (GDF-15) (Bootcov et al., 1997; Hromas et al., 1997; Lawton et al., 1997; Yokoyama-Kobayashi et al., 1997; Paralkar et al., 1998). Similar to other TGF-β-related cytokines, MIC-1 is synthesised as an inactive precursor protein, which undergoes disulphide-linked homodimerisation. Upon proteolytic cleavage of the N-terminal pro-peptide, mature MIC-1 is secreted as an approximately 24.5 kDa dimeric protein (Bauskin et al., 2000). Amino acid sequences for MIC-1 are disclosed in WO 99/06445, WO 00/70051, WO 01/81928, WO 2005/113585, Bottner et al. (1999b); Bootcov et al., 1997; Back et al., 2001; Hromas et al. (1997), Paralkar et al., 1998; Morrish et al., 1996; and Yokoyama-Kobayashi et al., (1997). The amino acid sequence for the common or "wild type" mature MIC-1 polypeptide is shown at FIG. 1:

MIC-1 is expressed in several tissues (Moore et al., 2000; Bottner et al., 1999a; Fairlie et al., 1999; Bauskin et al., 2006). For example, Northern blots of human tissues indicate the presence of small amounts of MIC-1 mRNA in the kidney, pancreas and prostate, and large amounts in the placenta (Moore et al., 2000; Fairlie et al., 1999). Further, serum MIC-1 levels have been shown to increase with age in normal, apparently healthy subjects. MIC-1 overexpression has been associated with cancer, particularly prostate cancer (Welsh et al., 2003), and high serum concentrations of MIC-1 are associated with the presence of metastatic disease (Welsh et al., 2003; Brown et al., 2006). Serum MIC-1 is also elevated in chronic inflammatory diseases and predicts atherosclerotic events independently of traditional risk factors. Serum MIC-1 levels are also increased in chronic kidney disease (CKD; Johen et al., 2007).

CKD (also known as chronic renal disease) is characterised by a progressive loss of renal function over a period of months or years through five stages. CKD is initially characterised by mildly diminished renal function with few overt symptoms, which can eventually progress through to the final stage, known as chronic kidney failure (CKF), chronic renal failure (CRF), or end-stage renal disease, that is characterised by a severe illness and usually requires some form of "renal replacement therapy" (eg dialysis or renal transplant). More than 15.5 million adults in the United States of America have moderately severe impairment of renal function, and more than 480,000 are receiving active treatment for end-stage renal disease with more than 100,000 new patients starting treatment annually. Of the patients receiving treatment in 2005, more than 80,000 died.

CKD patients tend to suffer from accelerated atherosclerosis (a chronic inflammatory disease affecting arterial blood vessels), and are more likely to develop cardiovascular disease than the general population. Increased levels of inflammatory markers such as C-reactive protein (CRP) are considered to be a risk factor for acute cardiovascular events for both end-stage renal disease patients and normal populations (Apple et al., 2004). End-stage renal disease is associated with anorexia, weight loss and cachexia. There is thought to be a link between malnutrition and inflammation in renal failure patients with the two conditions often coexisting.

Some patients with end-stage renal disease can survive indefinitely on dialysis; however, many patients are likely to die in the absence of a kidney transplant. Weight loss, a lowered body mass index (BMI) and elevated serum inflammatory markers are considered to be predictors of mortality. However, the contribution of malnutrition and inflammation to disease outcome and the nature of the link between them is ill-defined. There are currently no reliable prospective methods for determining which patients are likely to die in the absence of a kidney transplant, and it is accordingly difficult to determine patients for whom a kidney transplant may be life saving.

The present applicant investigated the relationship between MIC-1 and altered nutrition in CKD and found that MIC-1 levels has clinical utility for prognosing mortality in CKD. The present applicant has also realised that MIC-1 levels can advantageously provide a means for selecting an end-stage renal disease subject for a kidney transplant.

SUMMARY OF THE INVENTION

In a first aspect, the present invention provides a method of prognosing the likelihood of death of a chronic kidney disease (CKD) test subject from all cause mortality, the method comprising detecting an elevated amount of MIC-1 in a test body sample from said subject, wherein the elevated amount of MIC-1 is associated with an increased likelihood of death of the subject.

In a second aspect, the present invention provides a method of prognosing the likelihood of death of a CKD test subject from all cause mortality, the method comprising the following steps:
(i) determining the amount of MIC-1 in a test body sample from said subject; and (ii) comparing the amount of MIC-1 determined in step (i) with a reference amount of MIC-1 that is an elevated amount of MIC-1 associated with an increased likelihood of death of the subject;

such that when the amount of MIC-1 determined in step (i) is greater than or substantially equivalent to the reference amount, the subject has an increased likelihood of death, and when the amount of MIC-1 determined in step (i) is less than the reference amount, the subject has a decreased likelihood of death.

In a third aspect, the present invention provides a method of selecting an end-stage renal disease test subject for a kidney transplant, the method comprising detecting an elevated amount of MIC-11 in a test body sample from said subject, wherein the elevated amount of MIC-1 is associated with an increased likelihood of death of the subject in the absence of a kidney transplant.

The method of the third aspect preferably comprises the following steps:
(i) determining the amount of MIC-1 in a test body sample from said subject; and
(ii) comparing the amount of MIC-1 determined in step (i) with a reference amount of MIC-1 that is associated with an increased likelihood of death of the subject in the absence of a kidney transplant;

such that when the amount of MIC-1 determined in step (i) is greater than or substantially equivalent to the reference amount, the subject has an increased likelihood of death in the absence of a kidney transplant, and when the amount of MIC-1 determined in step (i) is less than the reference amount, the subject has a decreased likelihood of death in the absence of a kidney transplant.

In a fourth aspect, the present invention provides a method of assessing an end-stage renal disease test subject undergoing dialysis for tolerance of said dialysis, the method comprising detecting an elevated amount of MIC-1 in a test body sample from said subject, wherein the elevated amount of MIC-1 is associated with poor tolerance to dialysis.

The method of the fourth aspect preferably comprises the following steps:
(i) determining the amount of MIC-1 present in a test body sample from said subject; and
(ii) comparing said amount of MIC-1 determined in step (i) against an amount or a range of amounts of MIC-1 present in comparative body sample(s) taken from
    said test subject at an earlier time point(s) before or after commencement of said -dialysis, or
    end-stage renal disease control subject(s) with long term tolerance to dialysis, such that when the amount of MIC-1 determined in step (i) is an elevated amount compared to the amount or range of amounts of MIC-1 present in said comparative body sample (s), the subject is likely to have a poor tolerance to dialysis, and when the amount of MIC-1 determined in step (i) is less than or substantially equivalent to the amount or range of amounts of MIC-1 present in said comparative body sample (s), the subject is likely to tolerate dialysis; or
(iii) comparing said amount of MIC-1 determined in step (i) with a reference amount of MIC-1 that is associated with long term tolerance to dialysis, such than when the amount of MIC-1 determined in step (i) is in elevated amount compared to the reference amount of MIC-1, the subject is likely to have poor tolerance to dialysis, and when the amount of MIC-1 determined in step (i) is less than or substantially equivalent to the reference amount of MIC-1, the subject is likely to tolerate dialysis.

In a fifth aspect, the present invention provides a method of preventing death or reducing the risk of death in a CKD subject, particularly a CKD subject suffering from end-stage renal disease, comprising treating blood, plasma or serum of said subject so as to remove or inactivate MIC-1 present in said blood, plasma or serum.

BRIEF DESCRIPTION OF THE FIGURES

FIG. 3 provides Kaplan-Meier plot of (A) patients in a US cohort who completed no more than three years dialysis at time of censoring (n=140), stratified according to their MIC-1 median of 6.3 ng/ml (ie 6300 pg/ml; circles represent a MIC-1 level below 6300 pg/ml, squares represent a MIC-1 level above 6300 pg/ml), which significantly stratified patient mortality (p=0.0124); (B) the same group of patients stratified according to the top decile of serum MIC-1 level of 14.2 ng/ml (ie 14200 pg/ml; circles represent a MIC-1 level below 14200 pg/ml, squares represent a MIC-1 level above 14200 pg/ml) showing that patients with a serum MIC-1 level in the top decile (>14200 pg/ml) were at significantly increased risk of mortality (p=0.0038); (C) patients with serum MIC-1 levels in the top decile (>14.2 ng/ml, ie 14200 pg/ml) irrespective of time on dialysis (n=381) had a mortality rate of 50% (p=0.0040).

DETAILED DESCRIPTION OF THE INVENTION

The present applicant has found that MIC-1 is a predictor of mortality in chronic kidney disease (CKD).

Thus, in a first aspect, the present invention provides a method of prognosing the likelihood of death of a chronic kidney disease (CKD) test subject from all cause mortality, the method comprising detecting an elevated amount of MIC-1 in a test body sample from said subject, wherein the elevated amount of MIC-1 is associated with an increased likelihood of death of the subject.

As used herein, the term "MIC-1" encompasses monomers, homodimers and/or heterodimers of a MIC-1 polypeptide, as well as variants, subunits and fragments (eg degradation products or digestion products of the MIC-1) thereof. MIC-1 variants encompassed by the term include mature human MIC-1 proteins which comprise a polypeptide comprising an amino acid sequence differing from that shown at FIG. 1A by 1 to 3 amino acids due to an amino acid substitution, deletion and/or addition, and which preferably show substantially equivalent biological activity to the polypeptide comprising the amino acid sequence shown at FIG. 1A (as may be measured using the assay described by Hromas et al, 1997 and/or the test described by Kempf et al, 2007); one particular example is the D6 mature human MIC-1 variant described in WO 01/81928 (the entire content of which is herein incorporated by reference), which comprises the amino acid sequence shown at FIG. 1B. MIC-1 subunits and fragments encompassed by the term include subunits and fragments of the polypeptide comprising the amino acid sequence shown at FIG. 1A or FIG. 1B and which show substantially equivalent immunological and/or biological activity to those polypeptides.

Preferably, the MIC-1 detected in the method of the first aspect is mature human MIC-1 protein, D6 mature human MIC-1 variant protein and/or heterodimers thereof.

As used herein, the term "chronic kidney disease" and the abbreviation "CKD" are to be understood as referring to a condition characterised by the progressive and permanent loss of renal function over a period of months or years. Subjects with CKD frequently have other medical conditions such as cardiovascular disease (including atherosclerosis and ischaemic heart disease), hypertension, malnutrition, inflammatory disease and diabetes or combinations thereof. CKD is recognised to progress through five stages as described in Table 1. The stages can, in part, be characterised by measuring the "glomerular filtration rate" (GFR), which can be described as the flow rate of filtered fluid through the kidney.

TABLE 1

Stages of chronic kidney disease

| | |
|---|---|
| Stage 1 | Slightly diminished function; normal or increased GFR* (>90 mL/min/1.73 m$^2$); kidney damage is defined as pathologic abnormalities or markers of damage, including abnormalities in blood or urine test or imaging studies |
| Stage 2 | Mild reduction in GFR (60-89 mL/min/1.73 m$^2$); kidney damage is defined as pathologic abnormalities or markers of damage, including abnormalities in blood or urine test or imaging studies |
| Stage 3 | Moderate reduction in GFR (30-59 mL/min/1.73 m$^2$) |
| Stage 4 | Severe reduction in GFR (15-29 mL/min/1.73 m$^2$) |
| Stage 5 (end-stage renal disease) | Established kidney failure (GFR <15 mL/min/1.73 m$^2$), or receiving permanent renal replacement therapy |

In some embodiments, the CKD test subject suffers from stage 1 CKD, preferably stage 2 CKD, more preferably stage 3 CKD, still more preferably stage 4 CKD, and most preferably, stage 5 CKD.

In most cases, the subject will eventually undergo renal replacement therapy. The term "renal replacement therapy", as used herein, is to be understood as referring to some type of intervention that is capable of at least partially compensating for reduced renal function, for example, dialysis (including haemodialysis, peritoneal dialysis or haemofiltration), a kidney transplant, etc. However, it is also to be understood that the type of renal replacement therapies are not to be limited to the above examples, as other therapies may suffice as renal replacement therapies. Further, it is to be understood that the timing and intensity of renal replacement therapy may vary from subject to subject, depending on the disease progression and other medical factors associated with an individual subject, as well as standard operating procedures at various institutions (eg dialysis units). For example, some subjects may temporarily undergo dialysis prior to progressing to end-stage renal disease. In another example, the intensity of dialysis may vary from subject from subject (for example, some subjects may undergo dialysis twice a week, whilst some subjects may undergo dialysis daily). In most CKD subjects, indefinite renal replacement therapy will eventually be required to survive.

As used herein, the term "indefinite renal replacement therapy" is to be understood as referring to the situation where the renal replacement therapy is normally expected to be required for the remainder of the subject's life. At this point, the subject can usually be considered to be suffering from end-stage renal disease.

As used herein, the term "end-stage renal disease" is to be understood as referring to a condition characterised in Table 1, wherein the subject has permanently lost substantial renal function, for example, having a glomerular filtration rate below 15 ml/min/1.73 m$^2$, or the subject is receiving indefinite renal replacement therapy (eg dialysis such as haemodialysis or peritoneal dialysis).

As used herein, the term "likelihood of death" is to be understood as referring to the probability of premature death of the CKD subject as compared to the normal expectancy of survival of a healthy subject or other CKD subjects (ie CKD subjects with normal or reduced amounts of MIC-1). In some embodiments of the method of the present invention, the elevated amount of MIC-1 predicts an increased likelihood of death of the subject within a period of 10 years from the taking of the test body sample. In other embodiments, the elevated amount of MIC-1 predicts an increased likelihood of death of the subject within a period of 3 years from the taking of the test body sample. Moreover, in further embodiments, the elevated amount of MIC-1 predicts an increased likelihood of death of the subject within a period of 1 year from the taking of the test body sample.

The term "all cause mortality", as used herein, relates to the cause of death of the subject due to any medical cause; that is, the cause of death may be any cause other than accident or misadventure. Accordingly, the subject may die from, for example, renal failure, cardiovascular disease (including atherosclerosis and ischaemic heart disease), hypertension, malnutrition, inflammatory disease, diabetes, or complications thereof or a combination thereof. Preferably, death is due to a cause selected from the group consisting of renal failure, cardiovascular disease and inflammatory disease.

Prognosing the likelihood of death in a subject with CKD is advantageous as it may allow for life saving intervention. For example, prognosing mortality may facilitate the selection or prioritisation of subjects for whom a kidney transplant would be life saving. Additionally, or alternatively, it may indicate that a particular subject would benefit from an alteration in therapy in order to attempt to prolong his/her life. For example, the subject may benefit from additional renal replacement therapy (eg more frequent dialysis); or alteration of other therapies, for example, alteration of therapies that are intended to replicate kidney endocrine function (such as the replacement of erythropoietin and vitamin D3, and the administration of calcium, phosphate binders, etc), or alteration of therapies to control other associated diseases (such as hypertension, cardiovascular disease, diabetes, inflammatory disease, etc).

The term "test body sample" as used herein refers to a sample of a body fluid, separated cells (ie cells taken from the body and at least partially separated from other body components), a tissue or an organ. Samples of body fluids can be obtained by well known techniques, and tissue or organ samples may be obtained from any tissue or organ by, for example, biopsy. Separated cells may be obtained from a body fluid; tissue or organ by separating techniques such as centrifugation or cell sorting. Preferably, cell, tissue or organ samples are obtained from those cells, tissues or organs which express or produce MIC-1.

The test body sample for use in the method of the first aspect may, therefore, be preferably selected from whole blood, blood plasma, serum, buffy coat, urine, cerebrospinal fluid, seminal fluid, synovial fluid, a tissue biopsy and/or an organ biopsy. More preferably, the test body sample is selected from the group consisting of whole blood, blood plasma, serum and urine. Most preferably, the test body sample is serum.

The test body sample may be taken from the subject at various time points during the course of CKD. For example, a sample may be taken from the subject prior to the subject commencing a renal replacement therapy (eg dialysis) or before commencing an indefinite renal replacement therapy, and then again at one or more time points while the subject is receiving renal replacement therapy or indefinite renal replacement therapy.

The term "amount" as used herein encompasses the absolute amount of MIC-1, the relative amount or concentration of MIC-1 as well as any value or parameter which correlates or corresponds thereto, or can be derived therefrom, such as, for example, values or parameters comprising intensity signal values from all specific physical or chemical properties obtained from MIC-1 by direct measurements (eg intensity values in mass spectra or NMR spectra) or indirect measurements (eg response levels determined from biological read out systems in response to MIC-1 or intensity signals obtained from specifically bound ligands). It is to be understood that values correlating to the abovementioned amounts or parameters can also be obtained by standard mathematical operations well known to persons skilled in the art.

The amount of MIC-1 that may be regarded as an "elevated amount" of MIC-1 for the purposes of the present invention may vary according to any of a number of factors, for example, the particular body sample type used, the sex of the subject (nb. males subjects show a mean serum MIC-1 level higher than that of female subjects), the age of the subject, the body mass index (BMI) of the subject, the smoking status of the subject (nb. former smokers tend to show increased levels of serum MIC-1 compared to those who have never smoked, while current smokers tend to show even greater levels of serum MIC-1), any use of non-steroidal anti-inflammatory drugs (NSAIDs) (nb. NSAID use can be associated with increased serum MIC-1 levels, particularly in male subjects), the waist-to-hip ratio in female subjects (nb. elevated waist-to-hip ratio in women is associated with increased serum MIC-1 levels), the stage of CKD the subject is suffering from, when the test body sample is taken, and the predicted period of time in which the death is likely to occur in, whether the patient is already receiving renal replacement therapy, and the method used to detect the elevated amount of MIC-1. Persons skilled in the art would understand that the greater the elevated amount of MIC-1 detected in a subject, the greater the likelihood of death. However, persons skilled in the art will also understand that a subject receiving indefinite renal replacement therapy may have a lower serum MIC-1 level than a subject with CKD that is not receiving indefinite renal replacement therapy as, for example, dialysis may decrease the MIC-1 level in whole blood, blood plasma and serum samples.

An elevated amount of MIC-1 for the purposes of the present invention may be represented by an amount greater than a specific pre-determined amount such as, for example, a serum MIC-1 level greater than about 6000 pg/ml (or, in the case of a whole blood or blood plasma sample, a level that corresponds to a serum MIC-1 level greater than about 6000 pg/ml); for example, since serum comprises about 50-55% of whole blood, a whole blood MIC-1 level of about 3000 pg/ml approximately corresponds to a serum MIC-1 level of about 6000 pg/ml) or, preferably, a serum MIC-1 level greater than about 7000 pg/ml (or, in the case of a whole blood or blood plasma sample, a level that corresponds to a serum MIC-1 level greater than about 7000 pg/ml), more preferably, a serum MIC-1 level greater than 10000 pg/ml (or, in the case of a whole blood or blood plasma sample, a level that corresponds to a serum MIC-1 level greater then about 10000 pg/ml), and most preferably, a serum MIC-1 level greater than about 14000 pg/ml (or, in the case of a whole blood or blood plasma sample, a level that corresponds to a serum MIC-1 level greater than about 14000 pg/ml). In some embodiments, the MIC-1 level is (or corresponds to) a serum level of greater than about 6300 pg/ml, preferably greater than about 7400 pg/ml, more preferably greater than about 14200 pg/ml. In the above context, the term "about" is to be understood as referring to an amount that is ±25% of the stated amount, preferably ±20%, more preferably ±10%, more preferably ±5%, and most preferably ±2% of the stated amount.

An elevated amount of MIC-1 for the purposes of the present invention may also be represented by an increase in the amount of MIC-1 within a subject that is detectable by serial measurements. Accordingly, the amount of MIC-1 in a test body sample may be determined at different time points in the same subject. For example, the amount of MIC-1 in a test body sample may be detected at certain time intervals. The time intervals may be determined on a case-by-case basis according to the needs of the subject and may be, for example, three months, one year, three years, five years or ten years, but it is to be understood that the time intervals may be adjusted according to any relevant health and medical factors of the subject. An elevated amount of MIC-1 in a test body sample within a subject may, accordingly, be detected by comparing the amount of MIC-1 in a test body sample at a given time point with the amount of MIC-1 in the same test body sample at an earlier time point. In this manner, an elevated amount of MIC-1 can be detected by determining the increase in the amount of MIC-1 present in the test body sample within any given subject over time.

Thus, the elevated amount of MIC-1 in the test body sample may be detected by using serial measurement by:
(i) determining the amount of MIC-1 present in the said test body sample; and
(ii) comparing said amount of MIC-1 against an amount or a range of amounts of MIC-1 present in comparative body sample(s) taken from the same subject at an earlier time point;
wherein the amount of MIC-1 present in step (i) is elevated compared to the amount or range of amounts of MIC-1 present in said comparative body sample(s). Preferably, the subject did not suffer from CKD or suffered from a less advanced stage of CKD at the earlier time point.

Alternatively or additionally, the elevated amount of MIC-1 in the test body sample may be detected by comparison with a normal subject, for example, by
(i) determining the amount of MIC-1 present in the said test body sample; and
(ii) comparing said amount of MIC-1 against an amount or a range of amounts of MIC-1 present in comparative body sample(s) taken from normal subject(s);
wherein the amount of MIC-1 present in step (i) is elevated compared to the amount or range of amounts of MIC-1 present in said comparative body sample(s).

As used herein, the term "normal subject" refers to a subject who does not die from any cause other than accident or misadventure within 10 years of the taking of the comparative body sample(s). Preferably, the normal subject(s) are age-matched, wherein the normal subject(s) are within 10 years of the age of the subject from which the relevant test body sample has been taken. More preferably, the normal subject(s) are within 5 years of the age of the subject from which the relevant test body sample has been taken.

Alternatively, the elevated amount of MIC-1 in the test body sample may be detected by comparison with an end-stage renal disease subject, for example, by
(i) determining the amount of MIC-1 present in the said test body sample; and
(ii) comparing said amount of MIC-1 against an amount or a range of amounts of MIC-1 present in comparative body sample(s) taken from at least one other subject that has been diagnosed with end-stage renal disease;
such that when the amount of MIC-1 present in step (i) is increased compared to the amount or range of amounts of MIC-1 present in said comparative body sample(s), the test subject has an increased likelihood of death compared to the at least one other subject. Persons skilled in the art will also understand that when the amount of MIC-1 present in step (i) is decreased compared to the amount of MIC-1 or range of amounts of MIC-1 present in said comparative body sample(s), the test subject has a decreased likelihood of death compared to the at least one other subject. The at least one other subject is preferably age-matched within 10 years of the age of the subject from which the relevant test body sample has been taken. More preferably, the at least one other subject is within 5 years of the age of the subject from which the relevant test body sample has been taken. Preferably, the comparison of step (ii), in this case, is made against the mean serum MIC-1 level of a group of subjects diagnosed with end-stage renal disease.

The person skilled in the art will also appreciate that the amount of MIC-1 in the test body sample may also be compared to a data set comprising information in relation to the level of MIC-1 in any of the foregoing subjects or a population comprising same.

An elevated amount of MIC-1 for the purposes of the present invention may also be detected by comparison with a reference amount of MIC-1 that is known to be associated with an increased likelihood of death of a CKD subject (eg an end-stage renal disease subject), wherein the reference amount is an increased amount compared to the amount or a range of amounts of MIC-1 present in comparative body sample(s) taken from normal subject(s).

Accordingly, in a second aspect, the present invention provides a method of prognosing the likelihood of death of a CKD test subject from all cause mortality, the method comprising the following steps:
(i) determining the amount of MIC-1 in a test body sample from said subject; and
(ii) comparing the amount of MIC-1 determined in step (i) with a reference amount of MIC-1 that is an elevated amount of MIC-1 associated with an increased likelihood of death of the subject;
such that when the amount of MIC-1 determined in step (i) is greater than or substantially equivalent to the reference amount, the subject has an increased likelihood of death, and when the amount of MIC-1 determined in step (i) is less than the reference amount, the subject has a decreased likelihood of death.

The method of the second aspect may further comprise the step of:
(iii) establishing a prognosis based on the comparison of step (ii) such that when the amount of MIC-1 determined in step (i) is greater than or substantially equivalent to the reference amount, the subject has an increased likelihood of death, and when the amount of MIC-1 determined in step (i) is less than the reference amount, the subject has a decreased likelihood of death.

Preferably, the MIC-1 detected in the method of the second aspect is mature human MIC-1 protein, D6 mature human MIC-1 variant protein and/or heterodimers thereof. The elevated amount of MIC-1 may be as described above in respect of the first aspect. The test body sample may also be as described above in respect of the first aspect, however preferably, the test body sample is selected from the group consisting of whole blood, blood plasma, serum and urine.

The method of the second aspect enables the reference amount of MIC-1 to be used as a prognostic marker, wherein the amount of MIC-1 in the test body sample may be simply compared to that reference amount. However, the sensitivity and specificity of such a method may depend on more than just the analytical "quality" of the method; it may also depend on the definition of what constitutes an abnormal result. That is, typically, for any particular marker, the distribution of marker levels for subjects with and without a disease overlaps such that a diagnostic/prognostic test based on that marker will not absolutely distinguish a normal subject from a diseased subject with complete accuracy. Thus, in some embodiments, the method may further comprise calculating receiver operating characteristic (ROC) curves by, for example, plotting the value of the MIC-1 amount versus the relative frequency of that value in "normal" and "disease" populations. The area under an ROC curve calculated in this manner can then be used as a measure of the probability that the determined amount of MIC-1 in the test body sample will allow a correct prognosis of the likelihood of death. In addition, an ROC curve can even be used where, for whatever reason, the determined amount of MIC-1 may be considered as inaccurate, since so long as it is possible to rank results, an ROC curve can still be calculated; for example, the determined MIC-1 amounts from body samples from CKD subjects may be ranked according to degree (say 1=low, 2=normal, and 3=high)—this ranking can then be correlated to results in the normal subject population and an ROC curve created according to methods well known to persons skilled in the art (eg Hanley and McNeil, 1982).

In an embodiment of the method of the second aspect, the present invention provides a method for prognosing the likelihood of death of an end-stage renal disease subject. When used in relation to a subject suffering from end-stage renal disease, the prognosis achieved by the method may predict that the subject is unlikely to survive without a kidney transplant.

Accordingly, in a third aspect, the present invention provides a method of selecting an end-stage renal disease test subject for a kidney transplant, the method comprising detecting an elevated amount of MIC-1 in a test body sample from said subject, wherein the elevated amount of MIC-1 is associated with an increased likelihood of death of the subject in the absence of a kidney transplant.

In one embodiment the method of the third aspect may comprise the following steps:
(i) determining the amount of MIC-1 in a test body sample from said subject; and
(ii) comparing the amount of MIC-1 determined in step (i) with a reference amount of MIC-1 that is associated with an increased likelihood of death of the subject in the absence of a kidney transplant; such that when the amount of MIC-1 determined in step (i) is greater than or substantially equivalent to the reference amount, the subject has an increased likelihood of death in the absence of a kidney transplant, and when the amount of MIC-11 determined in step (i) is less than the reference amount, the subject has a decreased likelihood of death in the absence of a kidney transplant.

In another embodiment of the method of the third aspect, the elevated amount of MIC-1 in the test body sample is detected by using serial measurement by:
(i) determining the amount of MIC-1 present in the said test body sample; and
(ii) comparing said amount of MIC-1 against an amount or a range of amounts of MIC-1 present in comparative body sample(s) taken from the same subject at an earlier time point;
wherein the amount of MIC-1 present in step (i) is elevated compared to the amount or range of amounts of MIC-1 present in said comparative body sample(s).

In a further embodiment of the method of the third aspect, the elevated amount of MIC-1 in the test body sample is detected by comparison with a normal subject by:
(i) determining the amount of MIC-1 present in the said test body sample; and
(ii) comparing said amount of MIC-1 against an amount or a range of amounts of MIC-1 present in comparative body sample(s) taken from normal subject(s);
wherein the amount of MIC-1 present in step (i) is elevated compared to the amount or range of amounts of MIC-1 present in said comparative body sample(s).

The method of the third aspect may further comprise the step of:
(iii) selecting an end-stage renal disease subject for a kidney transplant based on the comparison of step (ii) such that when the amount of MIC-1 determined in step (i) is greater than or substantially equivalent to the reference amount, the subject is selected for a kidney transplant, and when the amount of MIC-1 determined in step (i) is less than the reference amount, the subject is not selected for a kidney transplant.

Preferably, the MIC-1 detected in the method of the third aspect is mature human MIC-1 protein, D6 mature human MIC-1 variant protein and/or heterodimers thereof. The elevated amount of MIC-1 may be as described above in respect of the first aspect, and may be, therefore, compared to a reference amount (as described above) in order to select an end-stage renal disease test subject for a kidney transplant, wherein the reference amount is known to be associated with an increased risk of death in the absence of a kidney transplant (ie such that when the determined amount of MIC-1 in the test body sample is greater than or substantially equivalent to the reference amount, the subject is selected for a kidney transplant, and when the determined amount of MIC-1 in the test body sample is less than the reference amount, the subject may not be selected for a kidney transplant). The test body sample may be as described above in respect of the first aspect, however preferably, the test body sample is selected from the group consisting of whole blood, blood plasma, serum and urine.

The present applicant has also realised that MIC-1 levels tend to be lower in CKD subjects that can tolerate long term dialysis.

In a fourth aspect, the present invention provides a method of assessing an end-stage renal disease test subject undergoing dialysis for tolerance of said dialysis, the method comprising detecting an elevated amount of MIC-1 in a test body sample from said subject, wherein the elevated amount of MIC-1 is associated with poor tolerance to dialysis.

The method of the fourth aspect preferably comprises the following steps:

(i) determining the amount of MIC-1 present in a test body sample from said subject; and
(ii) comparing said amount of MIC-1 determined in step (i) against an amount or a range of amounts of MIC-1 present in comparative body, sample(s) taken from
said test subject at an earlier time point(s) before or after commencement of said dialysis, or
end-stage renal disease control subject(s) with long term tolerance to dialysis,
such that when the amount of MIC-1 determined in step (i) is an elevated amount compared to the amount or range of amounts of MIC-1 present in said comparative body sample(s), the subject is likely to have a poor tolerance to dialysis, and when the amount of MIC-1 determined in step (i) is less than or substantially equivalent to the amount or range of amounts of MIC-1 present in said comparative body sample(s), the subject is likely to tolerate dialysis; or
(iii) comparing said amount of MIC-1 determined in step (i) with a reference amount of MIC-1 that is associated with long term tolerance to dialysis,
such than when the amount of MIC-1 determined in step (i) is an elevated amount compared to the reference amount of MIC-1, the subject is likely to have poor tolerance to dialysis, and when the amount of MIC-1 determined in step (i) is less than or substantially equivalent to the reference amount of MIC-1, the subject is likely to tolerate dialysis.

Preferably, the MIC-1 detected in the method of the fourth aspect is mature human MIC-1 protein, D6 mature human MIC-1 variant protein and/or heterodimers thereof. The test body sample may be as described above in respect of the first aspect, however preferably, the test body sample is selected from the group consisting of whole blood, blood plasma, serum and urine.

In accordance with the method of the fourth aspect, the amount of MIC-1 in a test body sample may be used to assess an end-stage renal disease subject undergoing dialysis for tolerance of said dialysis, wherein the determination of: an elevated amount of MIC-1 (in the test body sample) relative to, for example, one or more preferably age-matched, end-stage renal disease subject(s) with long term tolerance to dialysis, is associated with poor tolerance of the dialysis; a substantially equivalent or reduced amount of MIC-1 relative to, for example, one or more preferably age-matched, end-stage renal disease subject(s) with long term tolerance to dialysis, is associated with acceptable or good tolerance of the dialysis; and a substantially unchanged (ie stable) or reduced amount of MIC-1 relative to a MIC-1 amount determined at an earlier time point(s) before or after commencement of dialysis, is associated with acceptable or good tolerance of the dialysis.

The methods of the present invention may be conducted in vitro or ex vivo. However, preferably, the methods are conducted in vitro.

For in vitro methods, the amount of MIC-1 present in a test body sample may be readily determined by any suitable method including, for example, immunoassays such as enzyme-linked immunosorbant assay (ELISA), radioimmunoassay (RIA) or immunohistochemistry (eg with sectionalised samples of a tissue biopsy) using anti-MIC-1 antibodies or fragments thereof. Anti-MIC-1 antibodies and fragments thereof may be produced by any of the methods well known to persons skilled in the art. However, it is possible to detect and quantify the levels of MIC-1 using other methods well known to persons skilled in the art such as, for example, methods involving the detection of binding of MIC-1 to a MIC-1 receptor (eg as disclosed in WO 2009/21293), or any other ligands that may bind MIC-1 (eg fetuin as disclosed in WO 2005/99746). Particularly suitable methods for determining the amount of MIC-1 present in a test body sample are immunoassays utilising labelled molecules in various sandwich, competition, or other assay formats. Such immunoassays will develop a signal which is indicative for the presence or absence of MIC-1. Further, the strength of the signal generated by such immunoassays may be correlated directly or indirectly (for example, reversely proportional) to the amount of MIC-1 present in a sample. Other particularly suitable methods for determining the amount of MIC-1 present in a test body sample are methods comprising the measurement of a physical or chemical property specific for MIC-1 such as a precise molecular mass or nuclear magnetic resonance (NMR) spectrum. Such methods may, therefore, be conducted using biosensors, optical devices coupled to immunoassays, biochips, analytical devices such as mass-spectrometers, NMR-analysers, or chromatography devices. Further particularly suitable methods for determining the amount of MIC-1 present in a test body sample include micro-plate ELISA-based methods, fully-automated or robotic immunoassays (available, for example, on Elecsys® analysers (Roche Diagnostics Corporation, Indianapolis, Ind., United States of America), enzymatic Cobalt Binding Assay (CBA) (available, for example, on Roche-Hitachi analysers (Roche Diagnostics Corporation), and latex agglutination assays (available, for example, on Roche-Hitachi analysers). Still further examples of particularly suitable methods for determining the amount of MIC-1 present in a test body sample include methods involving precipitation (eg immunoprecipitation), electrochemiluminescence (ie electro-generated chemiluminescence), electrochemiluminescence sandwich immunoassays (ECLIA), dissociation-enhanced lanthanide fluoro immunoassay (DELFIA), scintillation proximity assay (SPA), turbidimetry, nephelometry, and latex-enhanced turbidimetry and nephelometry. Further methods well known to persons skilled in the art, such as gel electrophoresis, Western Blotting, and mass spectrometry, may also be used alone or in combination with other suitable methods as described above.

As such, the determination of the amount of MIC-1 in the test body sample may comprise the steps of (i) contacting MIC-1 with a specific ligand, (ii) optionally removing non-bound ligand, and (iii) measuring the amount of bound ligand. The bound ligand (which may be bound by covalent and/or non-covalent binding) will generate an intensity signal. As indicated above, the ligand may be selected from anti-MIC-1 antibodies or fragments thereof but might otherwise be any other ligands that may bind MIC-1 such as, for example, any compound (including peptides, polypeptides, nucleic acids, aptamers (for example nucleic acid or peptide aptamers), glycoproteins such as fetuin, and small molecules) that binds to MIC-1. However, preferably, the ligand is selected from anti-MIC-1 antibodies or fragments thereof (including polyclonal and monoclonal antibodies, as well as fragments thereof, such as Fv, Fab and F(ab)$_2$ fragments that are capable of binding MIC-1, and recombinant antibodies such as single chain antibodies (eg scFV antibodies)) and a MIC-1 receptor (eg as disclosed in WO 2009/21293) or fragment thereof comprising at least one binding domain that binds to MIC-1. Methods of preparing such ligands are well known to persons skilled in the art.

Preferably, the ligand binds specifically to MIC-1. As used herein, the term "specific binding" and grammatical equivalents means that the ligand should not bind substantially to (that is, substantially "cross-react" with) another peptide, polypeptide or substance present in the test body sample. Preferably, the specifically bound MIC-1 will be bound with at least 3 times higher, more preferably at least 10 times higher, and most preferably at least 50 times higher affinity than any other relevant peptide, polypeptide or substance. Non-specific binding may be tolerable, if it can still be distinguished and measured unequivocally, for example, according to its size on a Western Blot, or by the relatively higher abundance of MIC-1 in the sample, or if it can be controlled for using a negative control sample or a normal subject control sample.

The ligand may be coupled covalently or non-covalently to a label allowing detection and measurement of the ligand. Suitable labelling may be performed by any of the direct or indirect methods well known to persons skilled in the art. However, by way of brief explanation, direct labeling involves the coupling of the label directly (covalently or non-covalently) to the ligand, while indirect labeling involves the binding (covalently or non-covalently) of a secondary ligand to the ligand (ie "first ligand") wherein the secondary ligand should specifically bind to the first ligand and may be coupled with a suitable label and/or be the target (receptor) of tertiary ligand binding to the secondary ligand. The use of secondary, tertiary or even higher order ligands can be used to increase the signal. Suitable secondary and higher order ligands may include antibodies, secondary antibodies, and the well-known streptavidin-biotin system (Vector Laboratories, Inc, Burlingame, Calif., United States of America). The ligand may also be "tagged" with one or more tags well known to persons skilled in the art, which tags may then be targets for higher order ligands. Suitable tags include biotin, digoxygenin, His-Tag, glutathione-S-transferase, FLAG, Green Fluorescent Protein (GFP), myc-tag, Influenza A virus haemagglutinin (HA), maltose binding protein and the like. Where the ligand is a protein, peptide or polypeptide, the tag is preferably located at the N-terminus and/or C-terminus. Suitable labels include any labels that are detectable by an appropriate detection method such as, for example, gold particles, latex beads, acridan ester, luminol, ruthenium, enzymatically-active labels, radioactive labels, magnetic labels (for example, "magnetic beads", including paramagnetic and superparamagnetic labels), and fluorescent labels. Suitable enzymatically-active labels include, for example, horseradish peroxidase, alkaline phosphatase, β-galactosidase, luciferase and derivatives thereof. Suitable substrates for enzymatically-active labels to enable detection include di-amino-benzidine (DAB), 3,3'-5,5'-tetramethylbenzidine, 4-nitro blue tetrazolium chloride and 5-bromo-4-chloro-3-indolyl-phosphate (NBT-BCIP), available as a ready-made stock solution from Roche Diagnostics Corporation), CDP-Star™ (Amersham Biosciences Inc, Fairfield, Conn., United States of America), and ECF™ (Amersham Biosciences Inc). Suitable radioactive labels include $^{35}$S, $^{125}$I, $^{32}$P, $^{33}$P and the like. Radioactive labels can be detected by any of the methods well known to persons skilled in the art including, for example, a light-sensitive film or a phosphor imager. Suitable fluorescent labels include fluorescent proteins (such as GFP and its derivatives, Cy3, Cy5, Texas Red, Fluorescein, and the Alexa dyes (for example, Alexa 568)). The use of quantum dots as fluorescent labels is also contemplated.

In some embodiments, the amount of MIC-1 in a test body sample may be determined as follows: (i) contacting a solid support comprising a ligand for MIC-1 as described above with said test body sample comprising MIC-1 and thereafter (ii) measuring the amount of MIC-1 which has become bound to the support. Preferably, in such embodiments, the ligand is selected from the group of ligands consisting of nucleic acids, peptides, polypeptides, antibodies and aptamers, and, preferably, is provided on the solid support in an immobilised form. The solid support may be composed of any of the typical materials well known to persons skilled in the art including, inter alia, commercially available column materials, polystyrene beads, latex beads, magnetic beads, colloid metal particles, glass and/or silicon chips and surfaces, nitrocellulose strips, membranes, sheets, duracytes, wells and walls of suitable reaction trays such as 96-well plates and other plates, plastic tubes etc. The ligand used in such embodiments may also be bound to a suitable carrier such as glass, polystyrene, polyvinyl chloride (PVC), polypropylene, polyethylene, polycarbonate, dextran, nylon, amyloses, natural and modified celluloses, polyacrylam ides, agaroses and magnetite. The nature of the carrier can be either soluble or insoluble. Suitable methods for immobilising the ligand to the solid support are well known to persons skilled in the art and include, for example, ionic, hydrophobic, covalent interactions and the like. It is also contemplated to use "suspension arrays" (Nolan and Sklae, 2002), wherein a carrier such as a microbead or microsphere is present in suspension, and the array consists of different microbeads or microspheres, possibly labeled, carrying different ligands. Methods of producing such arrays, for example based on solid-phase chemistry and photo-labile protective groups, are well known to persons skilled in the art (see, for example, U.S. Pat. No. 5,744,305).

In some embodiments of the methods of the present invention, the test subject will be in need of renal replacement therapy. It is to be understood that the renal replacement therapy may be temporary or indefinite as described above.

The present applicant has found that the MIC-1 level can be used as an independent predictor of mortality. As used herein, the term "predictor of mortality" is to be understood as referring to a medical factor that can be measured or considered in a subject to determine the likelihood of death.

The term "independent predictor of mortality", as used herein, is to be understood as indicating that the factor (ie MIC-1 level) as able to predict the likelihood of death without considering any other factor (which may or may not be concurrently measured). Accordingly, in some embodiments of the methods of the first and second aspects, the elevated amount of MIC-1 is used as an independent predictor of mortality. However, such methods according to the present invention may alternatively be used in conjunction with other predictors of mortality. For example, the methods may be used in combination with BMI, interleukin-6 (IL-6) levels, C-reactive protein (CRP) levels and/or short telomere length (De Meyer et al., 2008) as predictors for mortality. Therefore, determining an amount of MIC-1 along with BMI and/or CRP and MIC-1 at or beyond predetermined levels, may be used to prognose the likelihood of death of a CKD subject.

The present applicant has additionally realised that serum MIC-1 levels in incident CKD subjects has an independent relationship with the subjective global nutritional assessment (SGA) score. Further, the role of MIC-1 in weight regulation (Johen et al., 2007), and the prominent involvement of MIC-1 in inflammatory processes (Brown et al., 2002b; Brown et al., 2007) indicate that other factors may be associated with serum MIC-1 concentrations. The present applicant has realised that MIC-1 levels in CKD subjects' is independently related to the fat component of BMI (FBMI), as well as fibrinogen levels and 8-hydroxydeoxyguanosine (8-OHdG) levels, indicating that serum MIC-1 is an important, and previously unrecognised, link between inflammation, oxidative stress, and reduced nutrition in renal failure, which are all considered determinants of mortality in end-stage renal disease.

Accordingly, the methods of the present invention may be used in conjunction with at least one other predictor of mortality selected from the group consisting of weight loss, a decreased BMI, a decreased FBMI, decreased SGA, history of diabetes, history of cardiovascular disease, and increased serum inflammatory marker levels (such as C-reactive protein (CRP) level and fibrinogen level) and oxidation marker levels (such as 8-hydroxydeoxyguanosine (8-OHdG)); wherein the at least one other predictor of mortality is at or beyond a pre-determined cut off point. Suitable pre-determined cut-off points for each of the above predictors of mortality to predict mortality will be well understood by persons skilled in the art.

In some embodiments of the methods of the present invention, the likelihood of death may be predicted using a hazard analysis. For example, the likelihood of death may be predicted using a parametric proportional hazard model, a semi-parametric proportional hazard model, a regression model, or a Poisson regression model. Such models, which are well known to persons skilled in the art, include the Cox proportional hazard model, the Weibull proportional hazard model, and the Cox regression model.

In a fifth aspect, the present invention provides a method of preventing (ie delaying) death or reducing the risk of death in a CKD subject, particularly a CKD subject suffering from end-stage renal disease, comprising treating blood (eg whole blood), plasma or serum of said subject (in vivo or ex vivo) so as to remove or inactivate MIC-1 present in said blood, plasma or serum.

A suitable in vivo treatment of blood may comprise administering an effective amount of a MIC-1 inhibitory agent such as those described in WO 2005/099746; the entire content of which is herein incorporated by reference.

A suitable ex vivo treatment of blood may consist in a method comprising the steps of:

(i) providing a suitable substrate for binding MIC-1;

(ii) treating blood, plasma or serum removed from a subject by contacting the blood, plasma or serum ex vivo with said substrate such that MIC-1 present in the blood, plasma or serum is bound to the substrate;

(iii) separating the treated blood, plasma or serum from the substrate; and thereafter (iv) returning the treated blood, plasma or serum to the subject.

Such a treatment is described in WO 2009/046495; the entire content of which is herein incorporated by reference.

In an embodiment of the present invention, the test subject is suffering from end-stage renal disease. Preferably, the test subject is in need of renal replacement therapy. In some embodiments, the test subject has been receiving renal replacement therapy for between 1 month and 30 years. Preferably, the test subject has been receiving renal replacement therapy for between about 1 month to about 10 years, more preferably from about 1 month to about 5 years. Even more preferably, the test subject has been receiving renal replacement therapy for about 3 years.

The invention is hereinafter described by way of the following non-limiting examples and accompanying figures.

EXAMPLES

Example 1

Patient Cohorts

Materials and Methods

Cohorts of incident haemodialysis patients (ie patients that have reached the stage of requiring dialysis but have not yet commenced such treatment) from Sweden (n=98) and established haemodialysis patients from the United States of America (n381) had serum MIC-1 and C-Reactive Protein (CRP)-4 levels and BMI measured at study entry. Serum CRP-4 (Dade Behring, Inc., Deerfield, Ill., United States of America) was determined as described in Brown et al. (2002a); and serum MIC-1 was determined as described below. Demographic information collected included age, sex, history of cardiovascular disease (CVD), history of diabetes mellitus (DM), height and weight. Additional markers of nutrition, body composition and inflammation were assessed in Swedish patients.

Swedish Cohort

Swedish patients were incident dialysis patients with end-stage renal disease enrolled in the dialysis program at the Karolinska University Hospital at Huddinge between 1997 and 2004. They are all included as participants in an ongoing prospective study, parts of which have previously been described (Axelsson et al., 2006). Patients were excluded from the study if they were less than 18 years or above 70 years of age, had clinical signs of acute infection, acute vasculitis or liver disease at the time of evaluation, or were unwilling to participate in the study. After an overnight fast, venous blood samples were drawn and stored at 70° C. for biochemical analyses. The glomerular filtration rate, as estimated by the mean of creatinine and urea clearance, was calculated from 24-h urinary samples (ie urine samples collected over the course of one day) using routine methods. Other biochemical analyses were performed using routine methods including measuring serum 8-hydroxydeoxyguanosine (8-OHdG; as a measure of oxidative stress), serum creatinine and albumin. Nutritional status was assessed by subjective global assessment (SGA) (Qureshi et al., 1998) using a questionnaire that included six different components: three subjective assessments performed by the patient concerning the patient's history of weight loss, incidence of anorexia, and incidence of vomiting; and three objective assessments performed by the evaluators that are based on the presence of muscle atrophy (MA), oedema and the loss of subcutaneous fat. The grading of MA was assessed by a specially trained nurse examining the temporalis muscle, the prominence of the clavicles, the contour of the shoulders (rounded indicates well-nourished; squared indicates malnutrition), visibility of the scapula, the visibility of the ribs, and interosseous muscle mass between the thumb and forefinger, and the quadriceps muscle mass. The signs of MA were scored as follows: 1, no signs of MA; 2, mild signs of MA; 3, moderate signs of MA; 4, severe signs of MA. This assessment was completed either at the time of, or within 1 week of, blood sample collection. Body mass index (BMI) was calculated as weight (kg)/height (m)$^2$. The lean component of BMI (ie LBMI) was estimated by dual energy X-ray absorptiometry (DXA) using the DPX-L device (Lunar Corporation, Madison, Wis., United States of America) as previously described (Kyle et al., 2003). The fat component of BMI (ie FBMI) was calculated as previously described (Kyle et al., 2003). Handgrip strength (HGS) was evaluated in both the dominant and non-dominant arms using the Harpenden Handgrip Dynamo-meter (Yamar, Jackson, Mich., United States of America). Handgrip strength was repeated three times and the highest value was recorded. Patient exposure was censored for renal transplant (n=48). Upon transplantation, patients were classified as alive from the time of study entry to transplantation and this served as the exposure time.

United States Cohort 381 haemodialysis patients with end-stage renal disease were recruited who were treated by chronic tri-weekly intermittent haemodialysis for at least 30 days at outpatient dialysis units throughout Minneapolis-St. Paul, Minn., from April 1998 to March 1999. A predialysis blood sample (ie a sample from before a regular tri-weekly dialysis session) was obtained from each patient. The patients studied were a subgroup of the original end-stage renal disease patient database reported previously (Apple et al., 2002) for whom adequate serum sample volumes (frozen at 70° C.) remained for additional biomarker analysis. Patient exposure was censored for renal transplant (n18), discontinuation of haemodialysis (n=1) and transfer of patient to another renal dialysis unit (n=16).

Statistical Analysis

Results are expressed as mean±standard deviation unless otherwise indicated with p<0.05 indicating significance. Cohorts were compared using unpaired t-test and chi-square analysis for continuous and categorical variables, respectively. As many values were not normally distributed, correlations between markers were calculated by Spearman's rank test. Differences in cumulative survival rates were compared between patients with varied MIC-1 levels. Exposure was computed from date of blood draw until date of death with censoring first for length of time interval of interest. In the Swedish and US cohorts, renal transplant led to the patient being classified as censored and exposure was calculated to time of transplant. Additionally, US patients transferred to another dialysis facility (n=16) were classified as censored and exposure time calculated to time of transfer. Unadjusted and adjusted relative risks (RRs) of death and 95% confidence intervals were estimated by use of Cox proportional hazard models. Adjusted RRs were estimated after first fitting models with variables identified in previous analyses as independent risk factors. Survival curves were computed by the Kaplan-Meier method and compared among risk stratification groups using the log-rank statistic. Analyses were done with StatView 5.0 software (SAS Inc, Cary, N.C., United States of America).

Determination of MIC-1 Serum Levels

MIC-1 serum levels were determined as described in Brown et al. (2002) using a MIC-1 sandwich ELISA. Briefly, the sandwich ELISA was established using the mouse monoclonal antibody (MAb) 26G6H6 (Brown et al., 2002a; Moore et al., 2000) for antigen capture and a sheep polyclonal antibody (PAb) 233B3-P for detection (Brown et al., 2002a). The optimum concentration of both antibodies was determined and then used for all subsequent studies. Ninety-six-well Maxisorp ELISA plates were coated with MAb 26G6H6 supernatant diluted 1:5 (final concentration was approximately 20 ng/mL) in coating buffer (0.1 mol/L carbonate in distilled water, pH 9.4-9.8) at 4° C. for 24 hours. ELISA plates were then washed three times with 300 µL/well 1% (wt/vol) bovine serum albumin (BSA) in phosphate buffered saline (PBS) for 2 h at 37° C. Recombinant human MIC-1 (rhMIC-1) standards, tissue culture supernatant, or patient serum were then added to the plates (100 µL/well) and incubated for 1 h at 37° C. The plates were washed three times, followed by addition of 100 µL/well of the sheep PAb 233B3-P diluted 1:5000 in antibody diluent (PBS containing 1% (wt/vol) BSA and 0.05% (vol/vol) Tween-20) and incubated for 1 h at 37° C. ELISA plates were then washed three times, and 100 μL/well of biotinylated donkey anti-sheep IgG diluted to 1:5000 Ab dil was added and incubated for 1 h at 37° C. The plates were washed four times, followed by the addition of 100 μL/well of peroxidase substrate (1 mg/mL o-phenylenediamine dihydrochloride, Sigma) in 0.05 mol/L phosphate-citrate buffer containing 0.014% $H_2O_2$, pH5.0 (Sigma). Colour development was allowed to proceed for 5-15 min and was terminated by the addition of 100 μL/well of 4N $H_2SO_4$. The absorbance was measured at 490 nm in a microplate reader. The concentration of human MIC-1 in the samples was determined by comparison with the rhMIC-1 standard curve. The standard curve was constructed using standard curve-fitting software supplied with the microplate reader (Pasteur Diagnostics). The concentration of rhMIC-1 in the standard curve was determined on the basis of a comparison of this standard to a master standard of highly purified recombinant MIC-1. The master standard protein concentration was determined by an average of eight estimations of total amino acid composition. All samples were assayed in triplicate on at least two occasions. Results are presented as the mean+/− SD.

Results

The clinical characteristics and demographic information available for both cohorts of patients are summarised in Table 2. Key measurements of BMI, serum MIC-1 and CRP levels were not significantly different between the two populations (p=0.5117, 0.9672 and 0.0902 respectively; unpaired t-test). All patients with CKD had serum MIC-1 levels above the normal range of 200-1150 pg/ml (Brown et al., 2003).

TABLE 2

Demographic and clinical measures

|  | US Cohort | Swedish Cohort |
| --- | --- | --- |
| Total | 381 | 98 |
| Age (years) | 61 ± 16 | 53 ± 13 |
| Sex |  |  |
| Male | 219 (57%) | 58 (59%) |
| Female | 162 (43%) | 40 (41%) |
| Diabetes mellitus | 176 (46%) | 28 (30%) |
| History of cardiovascular disease and/or clinical signs of ischaemic heart disease | 116 (30%) | 29 (30%) |
| CRP (mg/L) | 16.6 ± 24.9 | 12.0 ± 20.3 |
| MIC-1 (pg/ml) | 8345 ± 4996 | 8396 ± 3697 |
| BMI (Kg/m2) | 25.3 ± 5.6 | 24.9 ± 4.6 |
| Follow-up time (months) | 19.4 ± 8.5 | 66.4 ± 34.9 |
| Deaths | 108 (28%) | 36 (37%) |

Data is shown as absolute number (percentage) or mean (±SD)

Of the 98 Swedish patients, the mean age was 53 years, and 58 (59%) were male. Mean patient follow-up was 5.5 years (range: 1.2 years to 13.2 years), with a total of 36 deaths occurred during 319 patient-years of follow-up. A history of cardiovascular disease and/or clinical signs of ischaemic heart disease (angina pectoris) was present in 29 (30%) patients and 28 (30%) had diabetes mellitus, which was significantly less than in the cohort of patients from the United States of America (p=0.0023, chi-square analysis).

Of the 381 US patients, the mean patient age was 61 years, which was significantly older than the Swedish population (p<0.0001, unpaired t-test), and 58% were male. Diabetes and a history of coronary artery disease (CAD) were found in 46% and 30% of patients, respectively. The median number of years on dialysis was 2.0 years (range: 0.1-22 years). Mean patient follow-up was 1.6 years (range: 41 days to 3 years), with a total of 108 deaths occurring during 615 patient-years of follow-up.

Example 2

Serum MIC-1 is Related to Subjective Global Nutritional Assessment (SGA) in the Swedish Cohort Data regarding the US cohort has previously been published indicating that serum MIC-1 levels are negatively correlated with BMI (Johen et al., 2007). To further study the nutritional changes associated with elevated serum MIC-1 levels, the present applicant analysed data from Swedish patients, from whom nutritional information was available.

Results and Discussion

The SGA was segregated into normal (SGA=1, n=69) or abnormal (SGA>1, n=27) with data being unavailable for 2 patients. SGA was significantly related with S-creatinine (p=0.0050), BMI (p=0.0051), handgrip strength (p=0.0016 and serum MIC-1 level (p=0.0065). Patients with serum MIC-1 above the median (7430 pg/ml) were significantly more likely to have an abnormal SGA (p=0.0001, chi-square). Serum MIC-1 level above the median was independently associated with SGA in multivariate logistic regression (Table 3). This model was further adjusted for factors which may be associated with MIC-1, specifically, age (Brown et al., 2006, p=0.7024) and CRP-5 (Brown et al. 2002b, p=0.1840). No significant attenuation of the independent association of MIC-1 with SGA was observed.

TABLE 3

Multivariate logistic regression for SGA in the Swedish Cohort

|  | Beta | Standard error | P |
| --- | --- | --- | --- |
| MIC-1 (>7400 pg/ml) | 2.168 | 0.712 | 0.0006 |
| CRP (≥10 g/l) | 2.140 | 0.014 | 0.0034 |
| BMI (>24.15 kg/m$^2$) | −2.163 | 0.127 | 0.0047 |
| Creatinine (mg/dl) | −0.006 | 0.002 | 0.0003 |
| Age (years) | −0.011 | 0.030 | 0.7024 |

This independent relationship of serum MIC-1 levels to SGA, the role of MIC-1 in weight regulation (Joher et al., 2007) and the prominent involvement of MIC-1 in inflammatory processes (Brown et al., 2002b; Brown et al., 2007) suggested it would be of value to examine other factors that might be associated with serum MIC-1 concentrations.

Example 3

Serum MIC-1 Level is Related to Nutrition and Markers of Inflammation and Oxidative Damage in the Swedish Cohort The relationship between serum MIC-1 levels and circulating markers of inflammation (CRP, fibrinogen) and oxidation (8OHdG), muscle atrophy, BMI and age was examined.

Results and Discussion

As shown in Table 4, serum MIC-1 level was compared to the levels of circulating markers of inflammation (CRP, fibrinogen), oxidation (8-OHdG) and age in the Swedish population, as these factors may be indicators of mortality in end-stage renal disease. Initial univariate analysis using Spearman rank correlation testing demonstrated that serum MIC-1 levels are related to age ($\rho=0.252$, $p=0.0135$), CRP ($\rho=0.283$, $p=0.0056$), fibrinogen ($\rho=0.346$, $p=0.0018$), 8-OHdG ($\rho=0.308$, $p=0.0033$) and serum albumin ($\rho=-0.211$, $p=0.0388$). Serum MIC-1 level and muscle atrophy did not significantly associate as a continuous variable; however, a strong trend was observed between serum MIC-1 above median ($p=0.0514$). Similarly, serum MIC-1 level and BMI did not associate as a continuous variable; however, a strong trend was observed between a serum MIC-1 level above median and BMI ($p=0.0612$). Further, patients with a serum MIC-1 above the median were more likely to have a BMI less than 25 kg/m$^2$ ($p=0.025$). The fat component of BMI (ie FBMI) remained independently associated with MIC-1 serum levels ($p=0.0004$) as did fibrinogen ($p=0.0007$) and serum 8-OHdG ($p=0.0485$) levels when included in a backward stepwise multivariate logistic regression analysis. This analysis initially included all variables examined (Table 4) and excluded factors that were not significantly associated with serum MIC-1 in a step-wise fashion.

These results show that MIC-1 is independently related to FBMI, as well as fibrinogen and 8-OHdG, indicating that serum MIC-1 is an important, previously unrecognised link between inflammation, oxidative stress, and reduced nutrition in renal failure, which are all considered determinants of mortality in end-stage renal disease.

TABLE 4

Factors correlated with serum MIC-1 levels in the Swedish Cohort

| Variable | MIC-1 Rho | P | Beta | Standard error |
|---|---|---|---|---|
| Univariate Analysis Clinical Parameters | | | | |
| Age (years) | 0.266 | 0.0090 | | |
| GFR (ml/min) | −0.145 | 0.1799 | | |
| Univariate Analysis Nutritional Markers | | | | |
| s-creatinine (mg/dl) | 0.079 | 0.4488 | | |
| Handgrip strength (kg) | 0.001 | 0.9910 | | |
| BMI (kg/m$^2$) | −0.066 | 0.5164 | | |
| S-albumin (g/l) | −0.205 | 0.0405 | | |
| LBMI (kg) | 0.060 | 0.5802 | | |
| FBMI (kg) | −0.105 | 0.3309 | | |
| SGA | 0.275 | 0.0077 | | |
| Univariate Analysis Inflammatory and Oxidation Biomarkers | | | | |
| CRP (mg/l) | 0.301 | 0.0030 | | |
| Fibrinogen (g/l) | 0.343 | 0.0019 | | |
| Ferritin (g/l) | 0.198 | 0.0545 | | |
| 8-OHdG (ng/ml) | 0.308 | 0.0062 | | |
| Stepwise Multivariate Regression for Factors Associated with MIC-1 (pg/ml) | | | | |
| FBMI (kg/m$^2$) | | 0.0004 | −0.334 | 0.109 |
| Fibrinogen (g/L) | | 0.0007 | 0.774 | 0.264 |
| 8-OHdG (ng/ml) | | 0.0485 | 1.701 | 0.868 |
| | | | | ($r^2 = 0.235$) |

Example 4

Serum MIC-1 Predicts Mortality in Incident Haemodialysis Patients in the Swedish Cohort The present applicant sought to determine whether serum MIC-1 level was predictive of mortality in haemodialysis patients.

Results and Discussion

The 98 Swedish patients were categorised as being either above or below the MIC-1 median serum level (ie 7430 pg/ml). Kaplan-Meier analysis indicated that a MIC-1 serum level above the median is associated with a significantly increased mortality rate ($p=0.0105$, FIG. 2). During the observation period of more than 13 years, the survival rate for patients with serum MIC-1 levels above the median was 53% compared with a 73% survival rate for patients with serum MIC-1 levels below the median.

When serum MIC-1 level was included in a multivariate analysis with age, sex, BMI, CRP level, and a history of CVD/DM and GFR, serum MIC-1 level was among the strongest independent predictors of mortality ($p=0.01840$, multivariate Cox proportional hazards), while CRP level and BMI failed to be independently associated with mortality (Table 5). Consequently, serum MIC-1 level was the strongest serum marker predictor of mortality.

Patients with CKD often have protein energy wasting associated with significant inflammation as determined by elevated circulating inflammatory markers and markers of oxidative stress. Oxidative damage is thought to enable chronic inflammatory states seen in advanced CKD. In this cohort, serum MIC-1 is also related to BMI as well as the nutritional measure SGA, independently of BMI and CRP. Only a component of BMI, FBMI, fibrinogen and 8-OHDG, an in vivo measure of oxidative stress, are independently related to serum MIC-1 levels indicating that MIC-1 is a an important, previously unrecognised, link between oxidative stress, inflammation, reduced BMI and mortality in CKD. These results show that serum MIC-1 levels are significantly related to the circulating markers of inflammation and oxidative stress.

Accordingly, these results indicate that serum MIC-1 level can be used as a predictive marker of all cause mortality in end-stage renal disease. Having obtained these results, a second independent cohort was analysed to validate serum MIC-1 measurement as a predictor of mortality in end-stage renal failure.

TABLE 5

Multivariate Cox proportional hazard analysis of all cause mortality in incident and prevalent haemodialysis patients

| Variable | Adjustment | Hazard ratio | 95% CI | p |
|---|---|---|---|---|
| Swedish Cohort n = 98 MIC-1 pg/ml | | | | |
| 1 | Crude | 1.1 | 1.0-1.2 | 0.0227 |
| 2 | 1+ age, sex, GFR, CVD, Diabetes | 1.2 | 1.0-1.3 | 0.0149 |
| 3 | 2+ CRP, BMI | 1.2 | 1.0-1.3 | 0.0184 |
| Final model | | | | |
| MIC (pg/ml) | | 1.1 | 1.1-1.2 | 0.0184 |
| Age (1 year) | | 1.1 | 1.1-1.2 | <0.0001 |
| Sex (male) | | 0.5 | 0.2-1.3 | 0.1572 |
| Diabetes (presence) | | 3.1 | 1.2-8.0 | 0.0172 |
| CVD (presence) | | 1.7 | 0.8-3.8 | 0.1332 |
| GFR (1 ml/min) | | 1.1 | 0.9-1.4 | 0.3457 |
| CRP (1 mg/L) | | 1 | 1.0-1.0 | 0.635 |
| BMI (1 kg/m2) | | 1 | 1.1-0.9 | 0.4524 |

TABLE 5-continued

Multivariate Cox proportional hazard analysis of all cause mortality in incident and prevalent haemodialysis patients

| Variable | Adjustment | Hazard ratio | 95% CI | p |
|---|---|---|---|---|
| | US Cohort (n = 381) MIC-1 pg/ml | | | |
| 1 | Crude | 1.1 | 1.0-1.1 | 0.0047 |
| 2 | 1+ age, sex, DV, CVD, Diabetes | 1 | 1.0-1.1 | 0.0402 |
| 3 | 2+ CRP, BMI Final model | 1 | 1.0-1.0 | 0.1117 |
| MIC (pg/ml) | | 1 | 1.0-1.0 | 0.1117 |
| Age (1 year) | | 1 | 1.0-1.1 | <0.0001 |
| Sex (male) | | 1.1 | 0.7-1.7 | 0.6867 |
| Diabetes (presence) | | 1.7 | 1.1-2.5 | 0.0149 |
| CVD (presence) | | 1.1 | 0.8-1.1 | 0.5406 |
| DV* (days) | | 1 | 1.0-1.0 | 0.9826 |
| CRP (1 mg/L) | | 1.1 | 1.0-1.2 | 0.0006 |
| BMI (1 kg/m2) | | 0.9 | 0.9-0.9 | <0.0001 |

*DV = dialysis vintage

Example 5

Serum MIC-1 Level Predicts Mortality in the First Three Years of Dialysis

The present applicant investigated whether MIC-1 can predict mortality in prevalent dialysis patients.
Results and Discussion In contrast to the incident Swedish cohort, the US cohort had commenced dialysis at between 30 days and 22 years prior to serum MIC-1 measurement. It was found that the serum MIC-1 level was significantly related to dialysis vintage (DV) ($\rho=0.182$, $p=0.0004$) and BMI ($\rho=-0.224$, $p<0.0001$). However, only BMI was independently associated with MIC-1 in multivariate regression analysis ($p=0.0019$) when included with DV. Serum MIC-1 level predicted mortality in prevalent haemodialysis patients ($p=0.0047$, Table 5). Additionally, when serum MIC-1 level was adjusted for age, sex, DV and history of CVD/DM, serum MIC-1 remained an independent predictor of mortality at study completion ($p=0.0420$, Table 5). Further adjustment for CRP and BMI significantly attenuated the predictive power of MIC-1. In contrast with the results observed for the Swedish population, the median MIC-1 level in the prevalent USA population failed to independently predictive of mortality (data not shown). However, patients in this prevalent cohort were sampled after dialysis commenced, potentially altering serum MIC-1 concentration. Consequently, the relationship of serum MIC-1 level to mortality risk was examined with varied times on dialysis.

Figure 2:
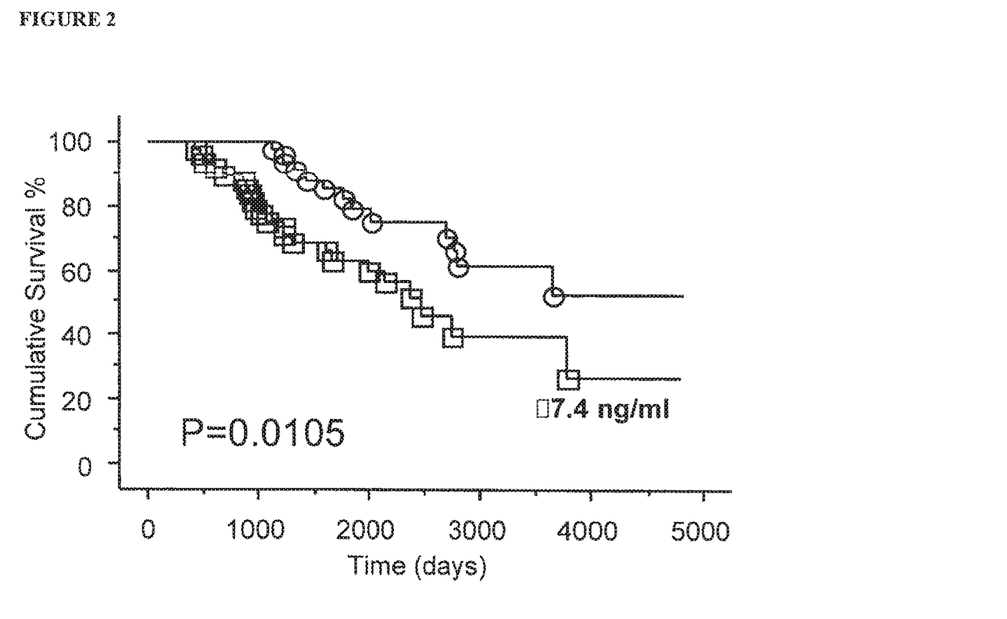
FIG. 2 provides a Kaplan-Meier plot of patients in a Swedish cohort (n=98) on dialysis from 1.2 to 13 years, showing that patients with serum MIC-1 levels greater than the median of 7.4 ng/ml (ie 7400 pg/ml; circles represent a MIC-1 level below 7400 pg/ml, squares represent a MIC-1 level above 7400 pg/ml) had significantly higher mortality than patients with serum MIC-1 levels below this level (p=0.0105)

In the incident Swedish renal failure patients, the association of relative risk of death for patients (adjusted for age, sex, GFR and history of CVD/DM) with serum MIC-1 levels was significant during the first three years following dialysis (for the whole cohort, RR=1.16, 95% CI=1.03-1.38; for patients with DV>1y, RR=1.16, 95% CI=1.03-1.38; for patients with DV>2y, RR=1.08, 95% CI=0.94-1.23; for patients with DV>3y, RR=0.98, 95% CI=0.82-1.17; FIG. 2). Similarly, in the 381 prevalent dialysis US patients, serum MIC-1 levels, following adjustment for age, sex, DV and history of CVD/DM, were also predictive of mortality in patients who had undergone three years or less of dialysis (for the whole cohort, RR=1.04, 95% CI=1.00-1.07; for patients with DV>1y, RR=1.04, 95% CI=1.01-1.08; for patients with DV>2y, RR=1.04, 95% CI=1.01-1.08; for patients with DV>3y, RR=1.03, 95% CI=0.98-1.10). In view of the predictive power of MIC-1 in the first three years after collection, in both the incident (ie Swedish cohort) and prevalent (ie US cohort) dialysis populations, the utility of serum MIC-1 levels to predict mortality in patients who had been on dialysis for three years or less in the prevalent US cohort was then examined.

Example 6

Figure 3:
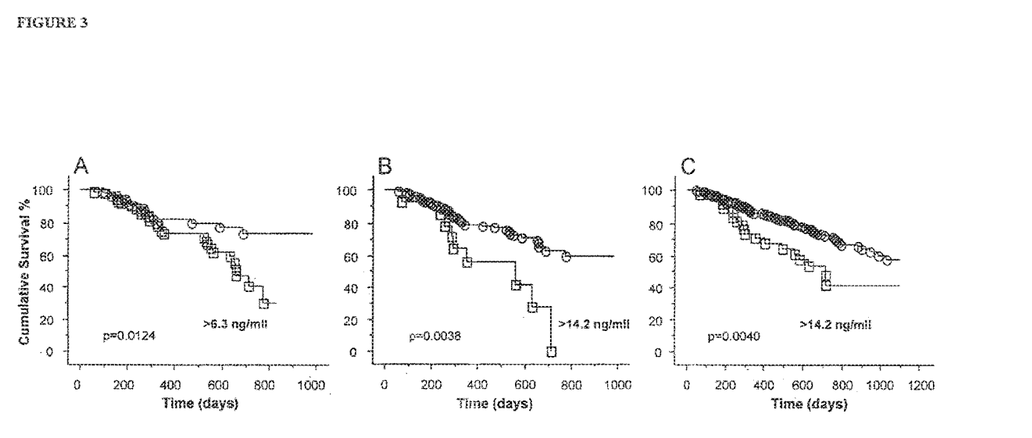

Serum MIC-1 is a Predictor of Early Mortality in End-Stage Renal Disease in the US Cohort The ability for serum MIC-1 levels to predict mortality in patients who had been on dialysis for three or less years was examined.
Results and Discussion Of the 149 prevalent dialysis patients from the US cohort on dialysis for three years or less at study completion, 46 died and serum MIC-1 level was found to be an independent predictor of mortality in multivariate analysis ($p=0.0320$, Table 6). Using Kaplan-Meier analysis, the patients with serum MIC-1 levels greater than the median (ie 6300 pg/ml) had an increased risk of mortality in the first three years ($p=0.0124$, FIG. 3A). When incident dialysis patients were compared to prevalent dialysis patients having three or less years dialysis, the patients undergoing dialysis had significantly lower serum MIC-1 medians (ie 7430 pg/ml for incident dialysis patients in the Swedish cohort compared to 6330 pg/ml for prevalent dialysis patients in the US cohort, $p=0.0136$) indicating that dialysis lowers MIC-1 serum levels. While not wishing to be bound by theory, it is reasoned that patients with serum MIC-1 levels in the top decile should be at a higher risk of mortality and that this would not be significantly affected by the institution of dialysis, and re-analysed results stratified for the top decile. Patients undergoing dialysis for less than three years with a serum MIC-1 level in the top decile (>14200 pg/ml) were found to be at a significantly increased risk of mortality ($p=0.0083$, FIG. 3B) and had a relative risk of mortality of 2.4 (95% CI 1.1-5.2) adjusted for age, CRP, BMI, history of DM and IHD. When the whole prevalent dialysis cohort was examined, patients in the top decile (>14200 pg/ml for the whole cohort), had a mortality rate of 50% ($p=0.0048$, FIG. 3C) and serum MIC-1 level greater than 142000 pg/ml remained an independent predictor of mortality (n=381, RR 1.9, 95% CI 1.1-3.2 when adjusted for age, CRP, BMI, history of DM and IHD and length of time on dialysis at study entry).

Thus, serum MIC-1 level is an additional predictor of mortality, appears to have a predictive power equal or superior to CRP and is independent of traditional markers. The predictive power of serum MIC-1 level was maintained in the first three years of dialysis in both cohorts. The test Swedish population was sampled prior to the institution of renal replacement therapy, had a lower number of diabetics and was younger, while the prevalent validation US cohort was sampled after institution of dialysis. These population differences are likely to have significantly affected the power of serum MIC-1 level to predict mortality in the US cohort, as indicated by the finding that dialysis institution was associated with lower serum MIC-1 levels. However, MIC-1 was validated as an independent marker of mortality in a prevalent dialysis population undergoing three or less years of dialysis. Accordingly, reduction in MIC-1 levels by dialysis institution should not significantly impact the effect of MIC-1 upon processes leading to mortality. Additionally, patients with serum MIC-1 levels in the top decile had significantly increased mortality regardless of time on dialysis.

TABLE 6

Multivariate Cox proportional hazard analysis of all cause mortality in prevalent dialysis patients undergoing three or less years of dialysis at study conclusion (n = 149)

| Variable | Adjustment | Hazard ratio | 95% CI | p |
|---|---|---|---|---|
| MIC-1 serum level (pg/ml) | | | | |
| 1 | Crude | 1.1 | 1.0-1.1 | 0.0025 |
| 2 | 1+ age, sex, CVD, Diabetes | 1.1 | 1.1-1.1 | 0.0102 |
| 3 | 2+ CRP, BMI | 1.1 | 1.0-1.2 | 0.0186 |
| Final model | | | | |
| MIC (pg/ml) | | 1.1 | 1.0-1.2 | 0.0186 |
| Age (1 year) | | 1.1 | 1.0-1.1 | <0.0001 |
| Sex (male) | | 0.7 | 0.4-1.4 | 0.3045 |
| Diabetes (presence) | | 1.1 | 0.6-2.1 | 0.6665 |
| CVD (presence) | | 1.9 | 0.9-3.6 | 0.0759 |
| CRP (1 mg/L) | | 1.1 | 1.0-1.2 | 0.0372 |
| BMI (1 kg/m2) | | 0.9 | 0.9-1.0 | 0.0186 |

Thus, the predictive value of serum MIC-1 level as a prospective marker of all cause mortality in both incident and prevalent dialysis patients has been demonstrated. Additionally, MIC-1 may be a mediator of inflammation, oxidative stress and cachexia in CKD. The incidence of CKD is steadily climbing and the demand for renal transplantation continues to exceed organ availability leading to significant morbidity and mortality in dialysis patients waiting for transplantation. Clearly, the ability to discriminate between those patients who will not tolerate dialysis for long periods offers a way to rationalise the allocation of organs.

Although a preferred embodiment of the method of the present invention has been described in the foregoing detailed description, it will be understood that the invention is not limited to the embodiment disclosed, but is capable of numerous rearrangements, modifications and substitutions without departing from the scope of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

REFERENCES

Apple, F S et al. Predictive value of cardiac troponin I and T for subsequent death in end-stage renal disease. *Circulation* 106:2941-2945 (2002).

Apple, F S et al. Multi-biomarker risk stratification of N-terminal pro-B-type natriuretic peptide, high-sensitivity C-reactive protein, and cardiac troponin T and I in end-stage renal disease for all-cause death. *Clin Chem* 50:2279-2285 (2004).

Axelsson, J et al. Are insulin-like growth factor and its binding proteins 1 and 3 clinically useful as markers of malnutrition, sarcopenia and inflammation in end-stage renal disease? *Eur J Clin Nutr* 60:718-726 (2006).

Baek, S J et al. Cyclooxygenase inhibitors regulate the expression of a TGF-beta superfamily member that has proapoptotic and antitumorigenic activities. *Mol Pharmacol* 59: 901-908 (2001).

Bauskin, A et al. The propeptide of macrophage inhibitory cytokine (MIC-1), a TGF-beta superfamily member, acts as a quality control determinant for correctly folded MIC-1. *Embo J* 19:2212-2220 (2000).

Bauskin, A R et al. Role of macrophage inhibitory cytokine-1 in tumourigenesis and diagnosis of cancer. *Cancer Res* 66(10):4983-4986 (2006).

Bootcov, M R et al. MIC-1, a novel macrophage inhibitory cytokine, is a divergent member of the TGF-beta superfamily. *Proc Natl Acad Sci USA*. 94(21):11514-9 (1997).

Bottner, M et al. Expression of a novel member of the TGF-beta superfamily, growth/differentiation factor-15/macrophage-inhibiting cytokine-1 (GDF-15/MIC-1) in adult rat tissues. *Cell Tissue Res* 297(1):103-110 (1999a).

Bottner, M et al. Characterization of the rat, mouse, and human genes of growth/differentiation factor-15/macrophage inhibiting cytokine-1 (GDF-15/MIC-1). *Gene* 237: 105-111 (1999b).

Brown, D A et al. Antibody-based approach to high-volume genotyping for MIC-1 polymorphism. *BioTechniques* 33:118-20, 122, 124 passim (2002a).

Brown, D A et al. Concentration in plasma of macrophage inhibitory cytokine-1 and risk of cardiovascular events in women: a nested case-control study. *Lancet* 359:2159-2163 (2002b).

Brown, D A et al. Serum macrophage inhibitory cytokine 1 in rheumatoid arthritis: A potential marker of erosive joint destruction. *Arthritis Rheum* 56:753-764 (2007).

Brown, D A et al. Measurement of serum levels of macrophage inhibitory cytokine 1 combined with prostate-specific antigen improves prostate cancer diagnosis. *Clin Cancer Res* 12:89-96 (2006).

Brown, D A et al. MIC-1 serum level and genotype: associations with progress and prognosis of colorectal carcinoma. *Clin Cancer Res* 9:2642-2650 (2003).

De Mayer, T et al. Studying telomeres in a longitudinal population based study. *Front Biosci* 13:2960-2970 (2008).

Fairlie, W D et al MIC-1 is a novel TGF-beta superfamily cytokine associated with macrophage activation. *J Leukoc Biol* 65(1):2-5 (1999).

Hanley, J A and B J McNeil. The meaning and use of the area under a receiver operating characteristic (ROC) curve. *Radiology* 143(1):29-36 (1982).

Hromas, R et al. PLAB, a novel placental bone morphogenetic protein. *Biochim Biophys Acta* 1354(1): 40-44 (1997).

Johnen, H et al. Tumor-induced anorexia and weight loss are mediated by the TGF-beta superfamily cytokine MIC-1. *Nat. Med* 13:1333-1340 (2007).

Kalantar-Zadeh, K and VS Balakrishnan. The kidney disease wasting: inflammation, oxidative stress, and diet-gene interaction. *Hemodial Int* 10:315-325 (2006).

Kempf, T et al. Circulating concentrations of growth-differentiation factor 15 in apparently healthy elderly individuals and patients with chronic heart failure as assessed by a new immunoradiometric sandwich assay. *Clin Chem* 53(2):284-291 (2007).

Kyle, U G et al. Body composition interpretation. Contributions of the fat-free mass index and the body fat mass index. *Nutrition* 19:597-604 (2003).

Lawton, L N et al., Identification of a novel member of the TGF-beta superfamily highly expressed in human placenta. *Gene* 203:17-26 (1997).

Moore, A G et al. The transforming growth factor-β superfamily cytokine macrophage inhibitory cytokine-1 is present in high concentrations in the serum of pregnant women. *J Clin Endocrinol Metab* 85(12):4781-4788 (2000).

Morrish, D W et al. Identification by subtractive hybridization of a spectrum of novel and unexpected genes associated with in vitro differentiation of human cytotrophoblast cells. *Placenta* 17:431-441 (1996).

Nolan, J P and L A Sklar. Suspension array technology: evolution of the flat-array paradigm. *Tends Biotechnol.* 20(1):9-12 (2002).

Nordfors, L et al. End-stage renal disease—not an equal opportunity disease: the role of genetic polymorphisms. *J Intern Med* 258:1-12 (2005).

Paralkar, V M et al. Cloning and characterization of a novel member of the transforming growth factor-beta/bone morphogenetic protein family. *J Biol Chem* 273 (22):13760-13767 (1998)

Qureshi, A R et al. Factors predicting malnutrition in haemodialysis patients: a cross-sectional study. *Kidney Int* 53:773-782 (1998).

Welsh, J B et al. Large-scale delineation of secreted protein biomarkers overexpressed in cancer tissue and serum. *Proc Natl Acad Sci USA* 100(6):3410-3415 (2003).

Yokoyama-Kobayashi, M et al. Human cDNA encoding a novel TGF-beta superfamily protein highly expressed in placenta. *J Biochem* 122(3):622-626 (1997).

The invention claimed is:

1. A method of treating a human subject with chronic kidney disease (CKD) for which the subject is receiving therapy, the method comprising:
 determining that the subject has an increased likelihood of death from all cause mortality within a period of 3 years by detecting an elevated amount of macrophage inhibitory cytokine (MIC-1) in a test serum or plasma sample from said subject as compared to the amount of MIC-1 in a sample from the subject at an earlier time point, and treating the subject by additional renal replacement therapy (RRT), administration of erythropoietin, vitamin D3, or calcium and/or phosphate binders, or kidney transplantation.

2. A method of treating a human subject with chronic kidney disease (CKD) for which the subject is receiving therapy, the method comprising:
 determining that the subject has an increased likelihood of death from all cause mortality within a period of 1 year by detecting an elevated amount of macrophage inhibitory cytokine (MIC-1) in a test serum or plasma sample from said subject as compared to the amount of MIC-1 in a sample from the subject at an earlier time point, treating the subject by additional renal replacement therapy (RRT), administration of erythropoietin, vitamin D3, or calcium and/or phosphate binders, or kidney transplantation.

* * * * *

SEQUENCE LISTING

```
<160> NUMBER OF SEQ ID NOS: 2

<210> SEQ ID NO 1
<211> LENGTH: 112
<212> TYPE: PRT
<213> ORGANISM: Homo sapiens

<400> SEQUENCE: 1

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 2
<211> LENGTH: 112
<212> TYPE: PRT
<213> ORGANISM: Homo sapiens

<400> SEQUENCE: 2

Ala Arg Asn Gly Asp Asp Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80
```

```
Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```